United States Patent [19]
Persinger

[11] Patent Number: 5,697,187
[45] Date of Patent: Dec. 16, 1997

[54] METHOD FOR TREATMENT OF CROPS BY AN IRRIGATION SOLUTION

[75] Inventor: James Persinger, Hugoton, Kans.

[73] Assignee: Oxlon, Inc., Hugoton, Kans.

[21] Appl. No.: 571,520

[22] Filed: Dec. 13, 1995

[51] Int. Cl.$^6$ .................. A01G 25/16; A01N 3/02
[52] U.S. Cl. .................. 47/58; 422/24; 422/28
[58] Field of Search ............... 47/1.4, 58, 58.01, 47/58.09, 58.1, 58.11, 58.12, 58.27, DIG. 10; 405/263; 422/24, 28; 210/760

[56] References Cited

U.S. PATENT DOCUMENTS

| | | | |
|---|---|---|---|
| 2,404,778 | 7/1946 | Allison | 204/314 |
| 2,704,274 | 3/1955 | Allison | 204/176 |
| 4,247,321 | 1/1981 | Persinger | 71/59 |
| 4,308,844 | 1/1982 | Persinger | 123/539 |
| 4,932,400 | 6/1990 | Persinger | 128/202.25 |
| 5,205,927 | 4/1993 | Wickramanayke | 210/170 |
| 5,269,943 | 12/1993 | Wickramanayke | 210/747 |
| 5,433,866 | 7/1995 | Hoppe et al. | 210/748 |
| 5,494,576 | 2/1996 | Hoppe et al. | 210/198.1 |
| 5,561,944 | 10/1996 | Ismail et al. | 47/58 |

FOREIGN PATENT DOCUMENTS

| | | | |
|---|---|---|---|
| 2171620 | 7/1987 | Japan | 47/58 |
| 2177845 | 7/1990 | Japan | 47/DIG. 10 |
| 3213198 | 9/1991 | Japan | 47/58 |
| 3219808 | 9/1991 | Japan | 47/1.4 |

Primary Examiner—James R. Feyrer

[57] ABSTRACT

The present invention provides a unique method and apparatus for improving crop yield through the use of an inventive irrigation solution to inhibit surface pathogens, improved water penetration and increase crop production and market quality. In a presently preferred embodiment, the inventive method comprises the steps of producing a gaseous mixture of ionized air including from about 50 parts per million to about 4,000 parts per million ozone, from about 1,000 parts per million to 20,000 parts per million oxygen, and from 1,100 to about 25,000 parts per million oxygen ions from ambient air; effecting direct contact between the ionized air gaseous mixture and a supply of water by means of a submicron injector to produce a gaseous solution for treatment of irrigation water to be applied to agricultural crops. Accordingly, by treating the crops during irrigation the inventive process is successful in stopping surface fungus and molds on plants above ground.

5 Claims, 2 Drawing Sheets

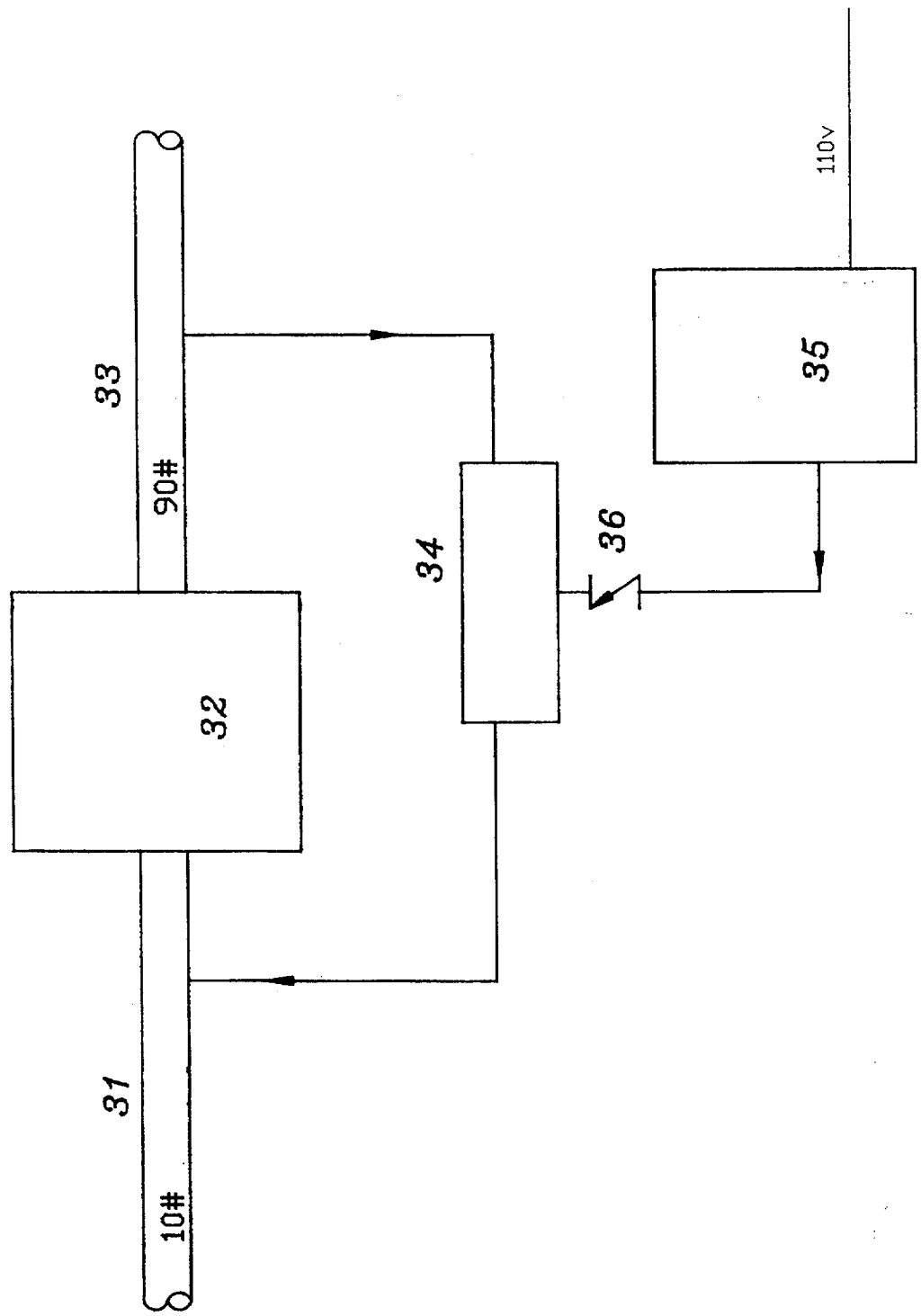

METHOD FOR TREATMENT OF CROPS BY AN IRRIGATION SOLUTION

BACKGROUND OF THE INVENTION

The subject invention relates to method and apparatus for improving crop yields through the use of and irrigation solution. This solution is successful in preventing surface fungus and molds on plants above ground, as well as blight on potato leaves, alternaria on carrot leaves, downy mildew on lettuce. Further, the invention improves crop yield and improves water penetration in soil. In more detail, the invention provides a unique method of enriching air with ozone, oxygen and oxygen ions within a prescribed range of irrigation for such crops.

In U.S. Pat. No. 4,932,400 the instant inventor disclosed a novel method and apparatus for inhibiting shipping fever in livestock which further improved digestibility of consumed feed. In more detail, the Persinger invention provided a unique method comprising the steps of producing a supply of ozone and nitrous oxide gas from ambient air; effecting direct contact between the ozone and nitrous oxide gas and a supply of water by means of a bubbler device to produce a prescribed hydrogen peroxide-nitrous oxide content; continuing such contact to a prescribed range and providing the resultant water supply for use as feed water to the livestock to be treated. Accordingly, by consumption of the unique resultant solution, the treated livestock was found to have increased digestibility of feed. Such treatment was further found to inhibit the growth of pathogenic organisms, thus inhibiting cattle disease such as shipping fever.

Crop-environment interactions are a very complex system and specific mechanisms are often hard to identify and isolate. Thus, occasional controversy over interpretations may occur; however, many facts are clear and beyond dispute. For example, when soils are depleted of essential inorganic nutrients readily identified deficiency symptoms usually appear. In other cases, such as with oxygen stress and the concurrent response to toxins that usually are produced, specific systems are more difficult to identify and isolate with present technology. It is commonly known that soil oxygen concentrations are in direct proportion to soil porosity and soil air content; thus, aeration is one variable that is directly affected by waterlogging (excess soil water). Waterlogging may occur naturally during a prolonged and intense rainfall or during excessive irrigation. Waterlogged conditions restrict the supply of oxygen to plant roots and to soil micro-organisms (microbes) by displacing the soil air and slowing oxygen diffusion; thus, creating anaerobic (without oxygen) soil conditions and producing soil gases that can be toxic to plant growth.

In soils, adequate exchangeable calciums (the active calcium) is necessary to maintain good soil structure. Total soil calcium content is not necessarily a good indicator of structural conditions that a soil may possess; so, many other factors must be taken into consideration. Soil structure and its particle size distribution determines porosity and the ability of the soil to hold and release water to growing plants in addition to the aeration (oxygenation) status. Thus, factors which affect soil structure are important variables in plant nutrition.

The rate of oxygen used by plant and microbe respiration in soil can be very large in comparison with the amount contained in the volume of soil usually occupied by root systems. Anaerobic conditions develop when roots and soil microbes use oxygen for respiration faster than it can enter the soil through its numerous interconnected soil pores and does not necessarily require that waterlogged conditions exist.

Plant roots and soil organisms obtain energy in a series of enzyme driven reactions involving the transfer of electrons (negatively charged particles) through the oxidation-reduction process with the ultimate production of water and carbon dioxide. If insufficient amounts of molecular oxygen are present, carbon dioxide formation is incomplete and toxic intermediates which are potentially harmful to plants are formed.

Since oxygen diffusion is 100,000 times slower in water than air, small increases in concentration can have a large effect on the amount of oxygen available for respiration. It is well known that nitrates and nitrogen dioxide are reduced to nitrogen gas through the action of denitrifying bacteria with the concurrent release of combined oxygen.

Accordingly, those skilled in the art have recognized a significant need to improve soil aeration thus enhancing plant nutrition. The present invention fulfills these needs.

SUMMARY OF THE INVENTION

The present invention provides an unique method and apparatus for improving crop yield through the use of an irrigation solution.

In a presently preferred embodiment, the method comprises the steps of:

a) producing a gaseous mixture of ionized air including from about 50 parts per million to about 4,000 parts per million ozone, from about 1,000 parts per million to 20,000 parts per million oxygen, and from 1,100 to about 25,000 parts per million oxygen ions from ambient air;

b) effecting direct contact between said gaseous mixture of ionized air derived from step a) and a supply of water by means of a submicron injector to produce a gaseous solution for treatment of crops;

c) continuing said contact between said gaseous mixture of ionized air and said water supply at a rate of 0.1 cfm to 2.0 cfm per 100 gpm of irrigation water;

d) providing the resultant gaseous solution to treat crops by means of an irrigation solution.

BRIEF DESCRIPTION OF THE DRAWING

FIG. 2 is a schematic block diagram of one embodied method for treatment of crops comprising a pressurized system including a booster pump and aspirator for obtaining prescribed amounts of ionized air, ozone and oxygen gasses in accordance with the present invention.

DESCRIPTION OF THE PREFERRED EMBODIMENTS

Figure 1:
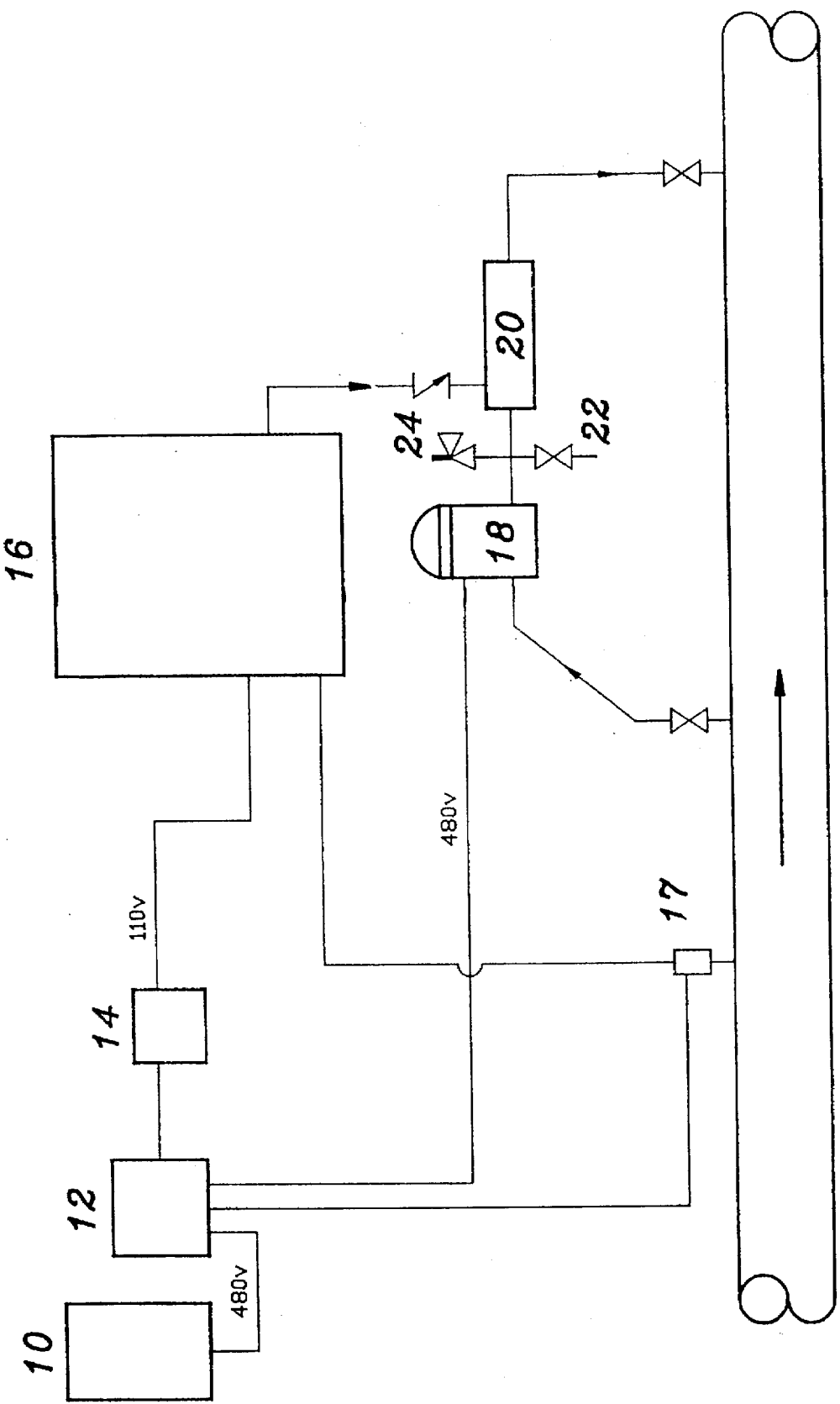
FIG. 1 is a schematic block diagram of one embodied method for treatment of crops comprising prescribed amounts of ionized air, ozone and oxygen gases in accordance with the present invention.

The present invention provides an unique method for treatment of crops by means of a unique irrigation solution.

In a presently preferred embodiment, the method comprises the steps of:

a) producing a gaseous mixture of ionized air including from about 50 parts per million to about 4,000 parts per million ozone, from about 1,000 parts per million to 20,000 parts per million oxygen, and from 1,100 to about 25,000 parts per million oxygen ions from ambient air;

b) effecting direct contact between said gaseous mixture of ionized air derived from step a) and a supply of water by means of a submicron injector to produce a gaseous solution for treatment of crops;

c) continuing said contact between said gaseous mixture of ionized air and said water supply at the rate of 0.1 cfm to 2.0 cfm per 100 gpm of irrigation water;

d) providing the resultant gaseous solution to treat crops by means of an irrigation solution.

FIG. 1 is a schematic block diagram of one embodied method for treatment of crops comprising of prescribed amounts of ionized air, ozone and oxygen gases in accordance with the present invention; and FIG. 1 depicts a schematic block diagram of one embodied method for treatment of crops by means of the inventive irrigation solution comprising prescribed amounts of ionized air, ozone and oxygen gases in solution in accordance with the present solution. In more detail, as shown in FIG. 1, an irrigation sprinkler breaker 10 is provided with a disconnect and fuse box 12 and electrically connected to transformer 14 for activating and controlling the ionization unit 16. The ionization unit 16 produces a gaseous mixture of ionized air including from about 50 parts per million to about 40,000 parts per million ozone, from about 1,000 parts per million to about 20,000 parts per million oxygen, and from about 1,100 to about 25,000 parts per million oxygen ions from ambient air. From the ionization unit 16, a direct contact is effected between the gaseous mixture derived from unit 16 which is regulated by pressure sensor 17 and fed through pump 18 to aspirator 20. The direct contact of the gaseous mixture of ionized air derived from unit 16 is admixed with a supply of water by means of a sub-micron injector to produce a gaseous solution for treatment of crops. The contact between the gaseous mixture of ionized air and the water supply is effected at a rate from about 0.1 cubic feet per minute to about 2.0 cubic feet per minute per 100 gallons per minute of water flow. Thereafter, the resultant gaseous solution is used to treat crops by means of an inventive irrigation solution in accordance with the present invention.

As shown in FIG. 2, for a pressurized system, the ionization unit 16 feeds the ionized air mixture to aspirator 20 which may be enhanced by means of booster pump 24 to achieve the desired end resultant solution.

In more detail, one suitable ozone generator means is disclosed in U.S. Pat. No. 4,308,844 issued to James Persinger on Jan. 5, 1982. The apparatus, shown in FIG. 2 of U.S. Pat. No. 4,308,844, comprises an ozone generator cell 24 which acts on ambient air supply. The generator cell 24 produces ozone, oxygen and oxygen ions in the air supply. The generator cell 24 comprises metallic plates 47 and 50 disposed adjacent to one another and separated from each other by a dialectic material 45 and an air gap 44.

A potential is induced across the adjacent plates 47 and 50 causing ionization of oxygen and nitrogen in the air flowing through the gap 44 which results in the production of ozone gas, nitrous oxide and ionizing air particles.

In accordance with the present invention, the generator cell 24 produces ozone, oxygen and oxygen ions within the air supply and induces a charge of the mixture by applying an alternating potential of 15,000 volts across the plates 47 and 50. The potential across gap 44, alternating at a frequency in a range from about 60 to 400 cycles per second, produces ozone gas, nitrous oxide and adds a charge to the air supply.

As described above, the present invention may comprise multiple generator cells, preferably twelve, sequentially connected to produce the desired amount of ionized oxygen.

One suitable ignition transformer for use with the ozone cell is available from Dongan Electric Manufacturing Company of Detroit, Mich. The specifications for the preferred ignition transformer is from about 5,000 volts to about 15,000 volts and preferably, has 15,000 volts production at 60 cycle.

If the ambient air is excessively wet, or contained polluting particulants, an air dryer and/or air filter may be used to remove excessive components prior to being fed into a compressor or air mover which flows the supply of air to the ozone generator cell.

Typically, the air supplied to the generator cells should have a minimum flow rate of about 4 cubic feet per minute per ozone generator cell. One suitable compressor for this purpose is commercially available from Gast Manufacturing of Bent Harbor, Mich.

ILLUSTRATIVE EXAMPLE

The inventive method is illustrated by the following representative treatment of crops by means of an irrigation solution.

Potatoes were grown under irrigation with the normal field practices accepted by potato growers except that the water was treated in accordance with the present invention. An electrically treated airstream which contained of ozone and charged radicals (ionization products) was injected into the water stream every minute during irrigation and field observations were made by the Grower. Similarly, a treated airstream was used to aerate the storage facilities where potato seed-stock is held for propagation and observations were made on the prevalence of tuber damage.

Significant improvements were noted in the field on water penetration and the total water requirements to produce the crop were reduced to approximately one-half of the previous requirements on the same field. Soil tests which were taken in preparation for next years crop reflects a large change in calcium levels. Infections of early blight were reduced very significantly without the usual use of fungicides. High yielding, high quality, high grading potatoes were delivered to the fresh pack storage facility with only 0.6 percent tare of clods.

Observations in storage showed a drastic reduction in the incidence of infected tubers. Improved growth characteristics were shown in the micro-propagation process. Based upon the reports of the grower and reports from others who observed the fields; and, proven principles of soil chemistry and plant physiology, the following conclusions were noted:

(1) Treatments in accord with the present invention made contributions to the production of potatoes. These observations are consistent with results where other tests were supported by more scientifically acceptable measurements.

(2) Treatments in accord with the present invention were observed to be beneficial to the storage of seed-stock and subsequent growth. These observations are consistent with known principles of physiology of plant cells under storage conditions.

I claim:

1. A method for improving crop yield through the use of an irrigation solution to inhibit surface pathogens and increase crop production and market quality of said crops, the method comprising the steps of;

a) producing a gaseous mixture of ionized air including from about 50 parts per million to about 4,000 parts per million ozone, from about 1,000 parts per million to 20,000 parts per million oxygen, and from 1,100 to about 25,000 parts per million oxygen ions from ambient air;

b) effecting direct contact between said gaseous mixture of ionized air derived from step a) and a supply of water by means of a submicron injector to produce a gaseous solution for treatment of crops;

c) continuing said contact between said gaseous mixture of ionized air and said water supply at the rate of 0.1 cfm to 2.0 cfm per 100 gpm of irrigation water; and d) providing the resultant gaseous solution to treat crops by means of an irrigation solution.

2. The method as defined in claim 1, wherein said gaseous mixture of ozone, oxygen and oxygen ion is produced by an ozone generator cell.

3. The method as defined in claim 1, wherein said gaseous mixture is produced by at least ten generator cells sequentially connected to produce said gaseous mixture.

4. The method as defined in claim 1, wherein the direct contact defined in step b) is through use of a Mazzei submicron injector at a rate of 100 gpm.

5. The method as defined in claim 1, wherein said resultant gaseous solution is used to irrigate one to six million pounds of crops.

* * * * *